(12) United States Patent
Bertetti et al.

(10) Patent No.: US 8,313,922 B2
(45) Date of Patent: Nov. 20, 2012

(54) PROCESS FOR THE PRODUCTION OF DAPTOMYCIN

(75) Inventors: Gianluca Bertetti, Rodano (IT); Antonella Malcangi, Rodano (IT); Roberto Muraca, Rodano (IT); Guido Trione, Rodano (IT); Alessia Rossi, Rodano (IT)

(73) Assignee: Antibioticos S.p.A., Rodano (IT)

( * ) Notice: Subject to any disclaimer, the term of this patent is extended or adjusted under 35 U.S.C. 154(b) by 501 days.

(21) Appl. No.: 12/512,414

(22) Filed: Jul. 30, 2009

(65) Prior Publication Data

US 2010/0047873 A1 Feb. 25, 2010

(30) Foreign Application Priority Data

Aug. 1, 2008 (EP) .................................... 08161630

(51) Int. Cl.
*C12N 1/20* (2006.01)
*C12P 1/04* (2006.01)
(52) U.S. Cl. ...................... 435/41; 435/170; 435/252.35
(58) Field of Classification Search ................. 435/170, 435/41, 252.35; 424/725
See application file for complete search history.

(56) References Cited

U.S. PATENT DOCUMENTS 4,885,243 A * 12/1989 Huber et al. ................. 435/71.3
* cited by examiner

*Primary Examiner* — Ruth Davis
(74) *Attorney, Agent, or Firm* — Arent Fox LLP

(57) ABSTRACT

The present invention relates to an improved process for the production of Daptomycin by fermentation with *Streptomyces roseosporus*, in the presence of n-decanal or *Cuphea* oil as sources of the n-decanoyl side chain. These reagents allow to reduce toxicity effects on the bacteria and to avoid the use of solvents in the feeding solution.

10 Claims, No Drawings

PROCESS FOR THE PRODUCTION OF DAPTOMYCIN

FIELD OF THE INVENTION

The present invention relates to an improved process for the production of Daptomycin by fermentation with *Streptomyces roseosporus*, using alternative sources of the n-decanoyl side chain.

BACKGROUND OF THE INVENTION

A-21978C$_{10}$, known as Daptomycin, is a 13-amino acids cyclic peptide antibiotic of formula (I)

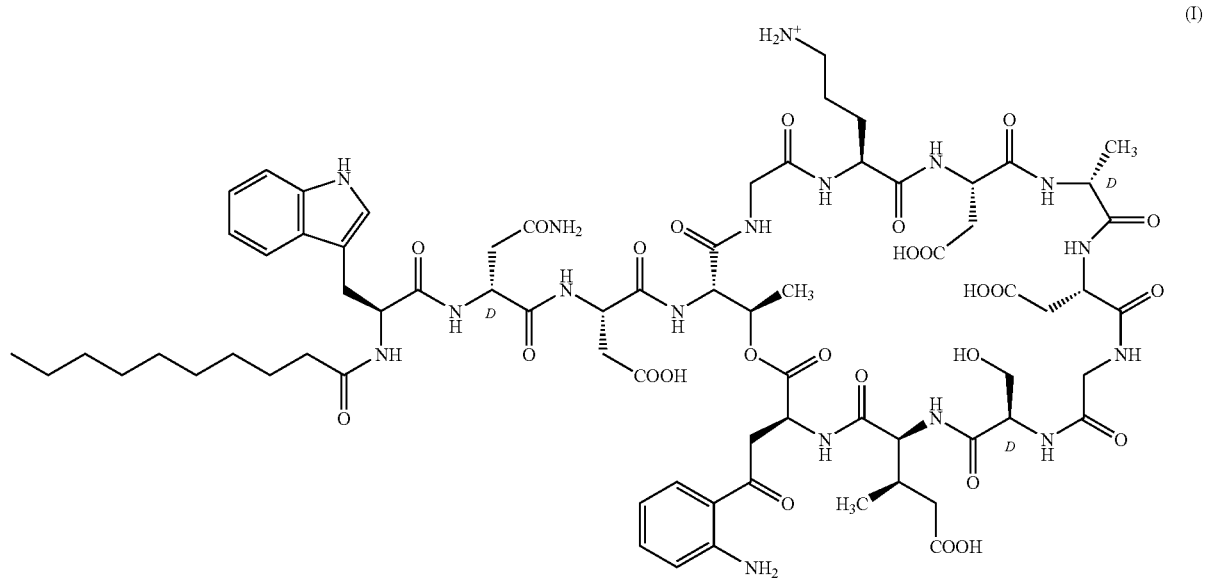

containing a n-decanoyl side chain linked to the N-terminal tryptophan.

Daptomycin is produced by submerged fermentation of *Streptomyces roseosporus*, in particular strains NRRL 11379 (ATCC 31568) and NRRL 15998, as well as any mutants, variants and recombinants thereof.

The production of Daptomycin in submerged culture was first disclosed in U.S. Pat. No. 4,331,594 and U.S. Pat. No. 4,800,157.

U.S. Pat. No. 4,885,243 discloses the preparation of Daptomycin by fed-batch fermentation, in which decanoic acid, used as source of the n-decanoyl side chain, is fed as a solution in an organic solvent, namely methyl oleate. The presence of the solvent in the feeding solution is necessary, because decanoic acid is a waxy solid at the fermentation temperature and only solutions containing at least 50% solvent are sufficiently fluid to be fed. Nevertheless, even in the presence of a solvent, at temperatures lower that 25° C. it is difficult to maintain a constant and homogeneous feeding, because decanoic acid may separate from the solution or form flakes and clumps. Decanoic acid exerts a toxic effect on the bacteria and for this reason the feeding rate must be kept under strict control.

DESCRIPTION OF THE INVENTION

It has now been found that the above-mentioned drawbacks can be overcome by using alternative sources of the n-decanoyl side-chain, namely decanal (n-decaldehyde, caprinaldehyde, capric aldehyde) or *Cuphea* oil. Accordingly, in a first embodiment, the present invention relates to a process for the preparation of Daptomycin by fermentation of *Streptomyces roseosporus* in the presence of n-decanal; in a second embodiment the invention relates to a process for the preparation of Daptomycin by fermentation of *Streptomyces roseosporus* in the presence of *Cuphea* oil. Particularly suitable *Streptomyces roseosporus* strains for carrying out the process are NRRL 11379 (ATTC 31568), NRRL 15998 and mutant B8.

In the first embodiment, n-decanal can be fed either as an organic solution in a suitable organic solvent, such as methyl oleate ethanol, ethyl acetate, preferably methyl oleate, or without solvents, because n-decanal is liquid at room temperature and separation of flakes or clumps formation does not occur.

*S. roseosporus* is in fact able to enzymatically convert the aldehyde to acid, which is then attached to the terminal N-tryptophan; it is pointed out that this conversion does not occur with different C10 sources, for example decanol. The use of n-decanal allows to increase productivity by 10% to 30% with respect to 50% decanoic acid+50% methyl oleate, probably due to the fact that this aldehyde is liquid, so it disperses in the fermentation broth and is more bioavailable. Furthermore, n-decanal is less toxic than n-decanoic acid: in fact, under the microscope, the mycelia appear less fragmented or vacuolized and this reduced toxicity allows to maintain a satisfactory production rate for a longer time.

In the second embodiment, *Cuphea* oil, either as such or dissolved in an organic solvent or mixed with another vegetable oil, is used. The *Cuphea* oil suitable for carrying out the invention can be derived from the seeds of several species of *Cuphea*, such as *C. lanceolata*, *C. viscosissima* and *C. koehneana* or hybrid species obtained therefrom. Suitable organic solvents are, for example, methyl oleate, ethanol, ethyl acetate, preferably methyl oleate; suitable vegetable oils are, for example soy oil, sunflower oil, palm oil; however, since *Cuphea* oil is fluid at room temperature, it is preferably fed in as such. *Cuphea* oil contains triglycerides with fatty acids of different length which are hydrolysed by the microorganism and used for the synthesis of Daptomycin. It was surprising found out that *Cuphea* oil has such a low toxicity on the microorganism that its accumulation in the fermentation is tolerated; therefore, unlike with decanoic acid/methyl oleate, strict control of the feeding rate is not necessary and the process can be carried out in batch, i.e. introducing all the substrate at the beginning of the fermentation; this means that a feeding tank, a feeding device and controls during addition are not required.

In the process of the invention, a carbon source necessary for the primary metabolism of the microorganism, like glycerol, can also be fed in together with n-decanal or *Cuphea* oil, thereby reaching a better equilibrium between the microorganism's growth and Daptomycin production.

It stems from the above that the process of the invention is advantageous on an industrial scale, as it is more convenient to carry out and cheaper, mainly due to the fact that the use of solvents can be avoided and that the carbon sources have a limited toxicity on the microorganism. The use of pure n-decanal in particularly advantageous in that the microorganism is fed with a 100% C10 source.

The invention will be illustrated in greater detail by means of the following examples.

EXAMPLES

Example 1

Decanal+Methyl Oleate

1A: *Streptomyces roseosporus* NRRL11379 in a 20 L Fermenter

A stock culture of *Streptomyces roseosporus* was stored under nitrogen, then used to inoculate a first vegetative fermentation phase. The seed medium, whose composition is reported in tables 1 and 2, was incubated in a 2 L round-bottom flask, containing 450 ml of broth, at 30° C. for 40 hrs on a rotating shaker with an agitation speed of 150 rpm.

TABLE 1

| Medium | |
|---|---|
| INGREDIENT | 1 L |
| Dextrose | 20 g |
| Soybean flour | 20 g |
| Yeast extract | 1 g |
| $KH_2PO_4$ | 0.22 g |
| $CaCO_3$ | 2 g |
| Saline solution | 2 ml |

No pH adjustment
Sterilization 121° C. × 20 min

TABLE 2

| Saline solution | |
|---|---|
| INGREDIENT | 100 ml |
| $FeSO_4$ | 0.2 g |
| HCl (37%) | 2 ml |
| $MgSO_4 \cdot 7H_2O$ | 10 g |
| KCl | 10 g |

Sterilization 121° C. × 20 min

At the end of the incubation the grown phase was used for seeding a production fermenter (20 L capacity, working volume 15 L) containing a medium having the following composition (Table 3).

TABLE 3

| Production medium | |
|---|---|
| INGREDIENT | g/L |
| Soybean flour | 22 |
| $Fe(NH_4)_2SO_4$ | 0.66 |
| pH adjusted to 7.0 | |
| $KH_2PO_4$ (optional) | 0.22 |
| Dextrose | 8.25 |
| Potato Dextrin | 33 |
| Molasses | 2.75 |
| Voranol | 0.8 |

Sterilization 121° C. × 45 min

The incubation of the production phase was carried out under the following conditions: 30° C., 1 vvm, stirring 150-350 rpm and back pressure 0.5 bar. The pH was maintained at 6.5 by addition of an ammonium hydroxide solution.

After 18 hrs, when the glucose concentration in the medium dropped below 3-4 g/L, the fermenter was fed with a solution containing 50% decanal and 50% methyl oleate (v/v) at a flow rate ranging from 3 to 7 ml/h.

Daptomycin production started after 40 hrs and reached a productivity of 0.6 g/L in 186 hrs.

1B: *Streptomyces roseosporus* NRRL11379 in a 1000 L Fermenter

*Streptomyces roseosporus* was stored under nitrogen. The stock culture was then used to inoculate the first vegetative fermentation phase. The preseed medium, whose composition is reported in table 4, was incubated in a two round-bottom flask (2 L), containing 450 ml broth, at 30° C. for 40 hrs on a rotating shaker with an agitation speed of 150 rpm.

TABLE 4

| Preseed medium | |
|---|---|
| INGREDIENT | 1 L |
| Bactotryptone | 17 g |
| Peptone | 3 g |
| NaCl | 5 g |
| $K_2HPO_4$ | 2.5 g |
| Dextrose | 2.75 g |
| Potato starch | 25 g |

No pH adjustment
Sterilization 121° C. × 20 min

At the end of the incubation the inoculum was used for seeding a second vegetative phase in a 100 L fermenter (working volume 60 L) containing a medium having the following composition (Table 5).

TABLE 5

| Seed medium | |
|---|---|
| INGREDIENT | 1 L |
| Dextrose | 22 g |
| Soybean flour | 20 g |
| Yeast extract | 1 g |
| $CaCO_3$ | 2 g |
| Voranol | 0.5 g |
| $FeSO_4 \cdot 7H_2O$ | 4 mg |
| $MgSO_4 \cdot 7H_2O$ | 200 mg |
| KCl | 200 mg |

No pH adjustment
Sterilization 121° C. × 30 min

The incubation of the seed phase was carried out under the following conditions: 30° C., 0.8 vvm, stirring 160 rpm and back pressure 0.8 bar and for a time ranging from 22 to 28 hrs.

At the end of the incubation the seed phase was used for the inoculum of the production phase in a 1000 L fermenter (working volume 600 L) containing a medium having the following composition (Table 6).

TABLE 6

Production medium

| INGREDIENT | g/L |
|---|---|
| Soybean flour | 22 |
| Fe(NH$_4$)$_2$SO$_4$*6H$_2$O | 0.7 |
| Voranol | 1 |
| pH adjusted to 7.0 | |
| Dextrose | 9.1 |
| Potato Dextrin | 33 |
| Molasses | 2.8 |

Sterilization 121° C. × 45 min

The incubation of the production phase was carried out under the following conditions: 30° C., 0.5 vvm, stirring 120-160 rpm and back pressure 0.7 bar.

The pH was maintained at 6.5 by addition of an ammonium hydroxide solution.

After 24 hrs, when the glucose concentration in the medium dropped below 3-4 g/L, the fermenter was fed with a feeding solution containing 50% decanal and 50% methyl oleate (v/v) at a flow rate ranging from 180 to 210 ml/h.

Daptomycin production started after 40 hrs and reached a productivity of 460 mcg/ml in 180 hrs (+15% vs. fermentation with decanoic acid).

Prolonging the fermentation from 180 hrs (productivity peak in the process with decanoic acid) until 230 hrs, a concentration of 545 mcg/ml was obtained (+36% vs. decanoic acid fermentation).

Microscopic observation of the mycelium did not show any fragmentation or vacuolization, which are the typical damages caused by decanoic acid.

1C: *Streptomyces roseosporus* Mutant B8 in a 1000 L Fermenter

A stock culture of *Streptomyces roseosporus* mutant B8 was maintained under liquid nitrogen and the stock culture was then used to inoculate the first vegetative fermentation phase. The preseed medium, whose composition is reported in table 7, was incubated in two round-bottom flasks (2 L) containing 450 ml of broth; at 30° C. for 48 hrs on a rotating shaker with an agitation speed of 150 rpm.

TABLE 7

Medium

| INGREDIENT | 1 L |
|---|---|
| Dextrose | 20 g |
| Yeast extract | 1 g |
| Bactotryptone | 17 g |
| Peptone | 3 g |
| FeSO$_4$*7H$_2$ | 4 mg |
| MgSO$_4$*7H$_2$O | 200 mg |
| KCl | 200 mg |
| CaCO$_3$ | 2 g |
| Voranol | 1.1 g |

No pH adjustment
Sterilization 121° C. × 20 min

At the end of the incubation the inoculum was used for seeding a second vegetative phase in a 100 L fermenter (working volume 60 L) containing a medium having the following composition (Table 8).

TABLE 8

Seed medium

| INGREDIENT | 1 L |
|---|---|
| Dextrose | 2.5 g |
| Potato dextrin | 25 g |
| Soy peptone | 20 g |
| K$_2$HPO$_4$ | 2.5 g |
| NaCl | 5 g |
| Antifoam | 1 g |

No pH adjustment
Sterilization 120° C. × 30 min

The incubation of the seed phase was carried out under the following conditions: 30° C., 0.8 vvm, stirring 160 rpm and back pressure 0.8 bar and a time ranging from 30 to 36 hrs.

At the end of the incubation the seed phase was used for the inoculum of the production phase in a 1000 L fermenter (working volume 600 L) containing a medium having the composition described in table 6.

The incubation of the production phase was carried out under the following conditions: 30° C., 0.5 vvm, stirring 120÷160 rpm and back pressure 0.7 bar.

The pH was maintained at 6.5 by addition of an ammonium hydroxide solution.

After 24 hrs, when the glucose concentration in the medium dropped below 3-4 g/L, the fermenter was fed with a solution containing 50% decanal and 50% methyl oleate (v/v) with a flow rate ranging from 140 to 160 ml/h.

The use of mutant B8 allowed to obtain a productivity of 1.3 g/L in 180 hrs and to reach a potency of 1.5 g/L in 230 hrs, with a constant production rate.

Example 2

Decanal+Glycerol

The inoculum was carried out as described in Example 1A.

At the end of the incubation the inoculum was used for seeding a production fermenter of 20 L capacity (working volume 15 L), containing a medium having the composition described in Table 3.

The incubation of the production phase was carried out under the following conditions: 30° C., 1 vvm, stirring 150-350 rpm and back pressure 0.5 bar. The pH was maintained at 6.5 by addition of an ammonium hydroxide solution. After 20 hrs, when the glucose concentration in the medium dropped below 3-4 g/L, the fermenter was fed with 100% decanal at a flow rate ranging from 2 to 7 ml/h.

A second feed solution containing glycerol was fed at the same time with a flow rate of 10 ml/h.

Daptomycin production started after 40 hrs and reached a productivity of 0.2 g/L in 160 hrs.

Example 3

*Cuphea* Oil+Methyl Oleate

The inoculum was carried out as described in Example 1A.

At the end of the incubation the inoculum was used for seeding a production fermenter of 20 L capacity (working volume 15 L) containing a medium having the composition described in Table 3. The incubation of the production phase was carried out under the following conditions: 30° C., 1 vvm, stirring 150÷350 rpm and back pressure 0.5 bar. The pH was maintained at 6.5 by addition of an ammonium hydroxide solution. After 18 hrs, when the glucose concentration in the medium was below 3-4 g/L, the fermenter was fed with a feeding solution containing 70% *Cuphea* oil and 30% methyl oleate at a flow rate of 3.6 ml/h.

The fermentation was carried out for 210 hrs when a productivity of 0.6 g/L of Daptomycin was reached.

Example 4

*Cuphea* Oil+Glycerol

The inoculum was carried out as described in Example 1A.

At the end of the incubation the inoculum was used for seeding a productive fermenter of 20 L capacity (working volume 15 L) containing a medium having the composition described in Table 3. The incubation of the production phase was carried out under the following conditions: 30° C., 1 vvm, stirring 150÷350 rpm and back pressure 0.5 bar. The pH was maintained at 6.5 by addition of an ammonium hydroxide solution.

After 20 hrs, when the glucose concentration in the medium was below 3-4 g/L, the fermenter was fed with 100% *Cuphea* oil at a flow rate of 2.5 ml/h. A second carbon source, glycerol, was fed during the fermentation.

The process was continued for 210 hrs and a productivity of 0.6 g/L of Daptomycin was reached.

Example 5

*Cuphea* Oil in Batch

The inoculum was carried out as described in Example 1A.

At the end of the incubation the inoculum was used for seeding a productive fermenter of 20 L capacity (working volume 15 L) containing a medium having the following composition (Table 9).

TABLE 9

| production medium | |
|---|---|
| INGREDIENT | g/L |
| Soybean flour | 22 |
| Fe(NH$_4$)$_2$SO$_4$ | 0.66 |
| pH adjusted to 7.0 | |
| Cuphea oil | 42 |
| Dextrose | 8.25 |
| Potato Dextrin | 33 |
| Molasses | 2.75 |
| Voranol | 0.8 |

Sterilization 121° C. × 45 min

In the production phase, the incubation was carried out under the following conditions: 30° C., 1 vvm, stirring 150-350 rpm and back pressure 0.5 bar. The pH was maintained at 6.5 by addition of an ammonium hydroxide solution.

The fermentation temperature was set so as to maintain a constant oxygen uptake rate from 20 hrs to the end of the process.

The raw materials present in the batch medium were sufficient to support microorganism growth and Daptomycin production.

The invention claimed is:

1. Process for the production of Daptomycin, comprising fermenting *Streptomyces roseosporus* in the presence of n-decanal or *Cuphea* oil, wherein the n-decanal or *Cuphea* oil provide a source for a n-decanoyl side chain group.

2. The process according to claim 1, comprising fermenting *Streptomyces roseosporus* in the presence of n-decanal.

3. The process according to claim 2 wherein n-decanal is provided in a solution in an organic solvent selected from the group consisting of: methyl oleate, ethanol and ethyl acetate.

4. The process according to claim 3 wherein the solvent is methyl oleate.

5. The process according to claim 2 wherein n-decanal is provided without solvents.

6. The process according to claim 1, comprising fermenting *Streptomyces roseosporus* in the presence of *Cuphea* oil.

7. The process according to claim 6 wherein *Cuphea* oil is provided in a solution in an organic solvent selected from the group consisting of: methyl oleate and ethanol or mixed with soy oil, palm oil or sunflower oil.

8. The process according to claim 7 wherein the organic solvent is methyl oleate.

9. The process according to claim 6 wherein *Cuphea* oil is provided without solvents.

10. The process according to claim 6 which is carried out as batch fermentation with pure *Cuphea* oil.

* * * * *